United States Patent
Davies et al.

(10) Patent No.: US 9,352,092 B2
(45) Date of Patent: May 31, 2016

(54) MEDICATED MODULE WITH INTEGRAL FLOW DISTRIBUTION SYSTEM

(75) Inventors: James Alexander Davies, Leamington Spa (GB); Steven Wimpenny, Leamington Spa (GB); Daniel Thomas De Sausmarez Lintell, Rugby (GB); Malcolm Stanley Boyd, Wellesbourne (GB); Naceur Rekaya, Leamington Spa (GB); Simon Lewis Bilton, Leamington Spa (GB); John David Cross, Northhampton (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1156 days.

(21) Appl. No.: 13/322,092

(22) PCT Filed: Jun. 1, 2010

(86) PCT No.: PCT/EP2010/057586
§ 371 (c)(1),
(2), (4) Date: May 17, 2012

(87) PCT Pub. No.: WO2010/139676
PCT Pub. Date: Dec. 9, 2010

(65) Prior Publication Data
US 2012/0220949 A1    Aug. 30, 2012

Related U.S. Application Data

(60) Provisional application No. 61/183,456, filed on Jun. 2, 2009, provisional application No. 61/331,913, filed on May 6, 2010.

(30) Foreign Application Priority Data

Jul. 25, 2009    (EP) .................................... 09009656

(51) Int. Cl.
*A61M 5/31*    (2006.01)
*A61M 5/32*    (2006.01)
(Continued)

(52) U.S. Cl.
CPC ........... *A61M 5/2448* (2013.01); *A61M 5/2466* (2013.01); *A61M 5/3294* (2013.01);
(Continued)

(58) Field of Classification Search
CPC ............ A61M 5/2448; A61M 5/3294; A61M 5/2466; A61M 5/1413; A61M 5/1409; A61M 5/16827; A61M 5/2066; A61M 5/31596; A61M 2005/2451; A61M 2005/31598; A61M 3/005; A61M 2039/0027; A61M 5/284; A61M 5/3297; A61M 5/34; A61M 5/31556; A61M 5/31525; A61M 2005/1787; A61M 2005/3142; A61M 2206/20; A61J 1/2096; A61J 2001/2065; A61J 1/2089; A61J 1/2065; A61J 1/20
See application file for complete search history.

(56) References Cited

U.S. PATENT DOCUMENTS 3,657,864 A    4/1972   Davis, Jr. et al.
4,581,016 A *  4/1986   Gettig ............... A61M 5/31596
                                                             604/88

(Continued)

FOREIGN PATENT DOCUMENTS

JP    H7-507700        8/1995
JP    2002542903 A    12/2002
(Continued)

OTHER PUBLICATIONS

European Search Report for EP Application No. 09009656, dated Dec. 7, 2009.

(Continued)

*Primary Examiner* — Bhisma Mehta
*Assistant Examiner* — Jenna Zhang
(74) *Attorney, Agent, or Firm* — McDonnell Boehnen Hulbert & Berghoff LLP (57) ABSTRACT

A medicated module for an injection system to co-deliver at least two medicaments is disclosed where a primary delivery device containing a primary medicament accepts a medicated module containing a single dose of a secondary medicament contained within a capsule having an integral flow distributor/distribution system and where both medicaments are delivered through a single hollow needle.

14 Claims, 5 Drawing Sheets

(51) Int. Cl.
*A61M 5/24* (2006.01)
*A61M 5/34* (2006.01)
*A61M 5/00* (2006.01)
*A61M 5/178* (2006.01)
*A61M 5/28* (2006.01)
*A61M 3/00* (2006.01)
*A61M 5/14* (2006.01)
*A61M 5/20* (2006.01)
*A61J 1/20* (2006.01)
*A61M 5/315* (2006.01)
*A61M 5/50* (2006.01)

(52) U.S. Cl.
CPC ............... *A61M5/3297* (2013.01); *A61M 5/34* (2013.01); *A61J 1/20* (2013.01); *A61J 1/2065* (2015.05); *A61J 1/2089* (2013.01); *A61J 1/2096* (2013.01); *A61M 3/005* (2013.01); *A61M 5/1407* (2013.01); *A61M 5/1409* (2013.01); *A61M 5/1413* (2013.01); *A61M 5/2066* (2013.01); *A61M 5/284* (2013.01); *A61M 5/31525* (2013.01); *A61M 5/31556* (2013.01); *A61M 5/50* (2013.01); *A61M 2005/1787* (2013.01); *A61M 2005/3142* (2013.01); *A61M 2206/20* (2013.01)

(56) References Cited

U.S. PATENT DOCUMENTS

| | | | |
|---|---|---|---|
| 5,124,133 A | | 6/1992 | Schoenrock |
| 5,281,198 A | * | 1/1994 | Haber .................. A61J 1/2093 604/191 |
| 5,385,547 A | | 1/1995 | Wong et al. |
| 5,547,471 A | * | 8/1996 | Thompson ............ A61J 1/2089 604/83 |
| 5,865,798 A | * | 2/1999 | Grimard ........... A61M 5/31596 604/218 |
| 7,387,623 B2 | * | 6/2008 | MacLeod ............... A61J 1/2093 206/219 |
| 2002/0138043 A1 | * | 9/2002 | Tanaka .............. A61M 5/31596 604/191 |
| 2004/0015128 A1 | * | 1/2004 | Taylor .................... A61M 5/282 604/92 |
| 2005/0277883 A1 | * | 12/2005 | Kriesel ............. A61M 5/14244 604/131 |
| 2006/0276755 A1 | * | 12/2006 | Sullivan ............... A61M 5/2448 604/187 |
| 2008/0177238 A1 | * | 7/2008 | Follman ................ A61M 5/326 604/263 |
| 2010/0082015 A1 | * | 4/2010 | Chebator ................ A61M 5/19 604/533 |
| 2012/0104045 A1 | * | 5/2012 | Chang ............... A61M 5/31596 222/145.5 |

FOREIGN PATENT DOCUMENTS

| | | |
|---|---|---|
| JP | 2008535636 A | 9/2008 |
| WO | 88/02265 | 4/1988 |
| WO | 93/20885 | 10/1993 |
| WO | 94/11056 | 5/1994 |
| WO | 0066214 A1 | 11/2000 |
| WO | 02/098543 | 12/2002 |
| WO | 2007027203 A2 | 3/2007 |
| WO | 2008/045956 | 4/2008 |
| WO | 2008154092 A1 | 12/2008 |

OTHER PUBLICATIONS

International Search Report and Written Opinion for International Application No. PCT/EP2010/057586, completed Jul. 1, 2010.
International Preliminary Report on Patentability for International Application No. PCT/EP2010/057586, completed Jul. 20, 2010.
Japanese Office Action for JP Application No. 2012-513589, mailed Jan. 6, 2015.
English Translation of JP 2012-513589, Notice of Reasons for Rejection.

* cited by examiner

MEDICATED MODULE WITH INTEGRAL FLOW DISTRIBUTION SYSTEM

CROSS REFERENCE TO RELATED APPLICATIONS

The present application is a U.S. National Phase Application pursuant to 35 U.S.C. §371 of International Application No. PCT/EP2010/057586 filed Jun. 1, 2010, which claims priority to U.S. Provisional Patent Application No. 61/183,456 filed on Jun. 2, 2009, European Patent Application No. 09009656.1 filed on Jul. 25, 2009, and U.S. Provisional Patent Application No. 61/331,913 filed on May 6, 2010. The entire disclosure contents of these applications are herewith incorporated by reference into the present application.

FIELD OF THE INVENTION

This disclosure relates to medical devices and methods of delivering at least two drug agents from separate reservoirs using devices having only a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Our invention may be of particular benefit where the therapeutic response can be optimized for a specific target patient group, through control and definition of the therapeutic profile. More specifically our invention relates to a medicated module designed for use with a drug delivery device, where the medicated module contains a capsule of a secondary medicament. In one embodiment, this capsule is configured to ensure greater than about 80% expulsion of the secondary medicament during dose delivery.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two or more active medicaments or "agents" simultaneously. The two or more active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or patient or user.

Additional problems arise where a multi-drug compound therapy is required, because many users cannot cope with having to use more that one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple for the user to perform. In specific embodiments, our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Moreover, in specific embodiments, the opportunity is given for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

These and other advantages will become evident from the following more detailed description of the invention.

SUMMARY

The general problem to be solved by the present invention is to provide a medicated module, a drug delivery system and a method where the administration of a medicament is facilitated.

In specific embodiments, our invention allows complex combinations of multiple drug compounds within a single drug delivery system. In particular, a user may be enabled to set and dispense a multi-drug compound device through one single dose setting mechanism and a single dispense interface. This single dose setter may control the mechanism of the device such that a predefined combination of the individual drug compounds is delivered when a single dose of one of the medicaments is set and dispensed through the single dispense interface. The term drug dispense interface may be, in the context of this disclosure, any type of outlet that allows the two or more medicaments to exit the drug delivery system and be delivered to the patient. In a preferred embodiment the single drug dispense interface comprises a hollow needle cannula.

By defining the therapeutic relationship between the individual drug compounds our delivery device may help ensure that a patient/user receives the optimum therapeutic combination dose from a multi-drug compound device without the inherent risks associated with multiple inputs where the user has to calculate and set the correct dose combination every time they use the device. The combination of the individual medicaments comprises preferably at least two different drug agents, wherein each medicament comprises at least one drug agent. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect, this invention may be of particular benefit to users with dexterity or computational difficulties as the single input and associated predefined therapeutic profile may remove the need for them to calculate their prescribed dose every time they use the device and the single input may allow considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyhepta-decanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H -His-Gly-Glu-Gly-Thr-Phe-Thr-Ser-Asp-Leu-Ser-Lys-Gln-Met-Glu-Glu-Glu-Ala-Val-Arg-Leu -Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu -Glu-Glu-Ala-Val-Arg-Leu-Phe-Ile-Glu-Trp-Leu-Lys-Asn-Gly-Gly-Pro-Ser-Ser-Gly-Ala-Pro -Pro-Ser-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In specific embodiments, our invention is aimed at efficiently expelling or flushing the secondary medicament from the medicated module such that at least about 80%, preferably greater than 90%, is expelled from the medicated module through the single dispense interface. In some instances there may be a minimum dose of the first medicament that must be delivered to a patient. In those situations, it is important that the "flush through" performance of the system be as high as possible to expel substantially all of the second medicament when the lowest dose of the first medicament is set by the user. Our initial studies show that by minimizing the volume of the second reservoir the theoretical "flush through" performance increases. For example, decreasing the volume of the second reservoir from 40 micro liters to 25 micro liters and dispensing a 2 unit dose of the first medicament will increase the flush through of the second medicament from about 50% to about 80%.

Preferably the secondary medicament is expelled with a minimum of mixing with the primary medicament. This can be accomplished by designing the medicated module with a capsule having an integral flow distribution device or a collection of separate parts defining a flow distribution system. The terms "flow distributor," "flow distribution device," and "flow distribution system" are used interchangeably in this application and are meant to include all flow configurations that increase the expulsion of the second medicament from the medicated module, preferably to a level of at least about 80%. In some cases the flow distribution system may be a single component and in other embodiments it may be a collection of components, such as ribs, spirals, grooves, or channels that are defined using various structures in the medicated module.

One embodiment of our medicated module attachable to a drug delivery device comprises a housing having a proximal end and a distal end, where the proximal end has a connector configured for attachment to a drug delivery device. The medicated module comprises a capsule containing a medicament. The capsule may have top and bottom seals, for example, induction seals, septum or other pierceable seals. The contained medicament may be a single dose of a medicament. Moreover, a flow distribution system is contained in the capsule. The flow distributor may minimize stagnant flow of the medicament and promote/maximize plug flow of the medicament through the capsule and out of the medicated module.

The septa are preferably fixed to the capsule using ferrules or other septa retaining means, similar to those traditionally used to secure a rubber septum in a standard multi-dose cartridge. In other embodiments the septa could be fixed in a number of alternate ways such as mechanical friction fit and non-mechanical bonding and the like. The septa can be comprised of rubber, polymer, or any other material that allows piercing by a hollow needle and that can be used to achieve an appropriate seal with the main body of the capsule. Preferably, the capsule contains a glass vial or other type of vial made from a material that is capable of containing the medicament stored in the capsule (either independently or in combination with other components or over wraps and the like).

The flow distributor can be any structure or collection of structures/features that causes radial and/or annular and/or axial and/or circumferential/swirl flow of the medicament and significantly reduces or prohibits back mixing from occurring, and/or stagnant zones from forming. Preferably, the flow distributor is a cylindrical pin having two or more support ribs or flow grooves defining one, two, or more medicament flow channels. Preferably the flow distributor comprises one or more radial vanes. The use of the flow distributor also greatly improves the efficiency related to the filling of the capsule during manufacture of the capsule and/or medicated module generally.

In a further embodiment the flow distributor and the vial may be provided as a one-piece component, e.g. as a one-piece molded component. Alternatively the flow distributor and the vial may render a one-piece component utilizing e.g. design principles such as form fit, force fit or material fit, such as welding, gluing, or the like, or any combination thereof. The one-piece component may comprise one, two, or more medicament flow channels, preferably one flow channel.

The medicated module preferably contains a capsule that is a sterile self-contained sealed reservoir of a (secondary) medicament. The capsule could also be replaceable. Preferably the capsule contains a liquid medicament, most preferably comprising a glucagon-like peptide-1 (GLP-1). In some cases, it is preferred that the capsule contains a liquid medicament comprising a mix of at least two drug agents, for example, a mix of a glucagon-like peptide-1 (GLP-1) and insulin.

Another embodiment covers a medicated module where a first needle is fixed in the proximal end of the module housing. The first needle may be fixed within a retention cap positioned in the proximal end of the module housing. A second needle is fixed within the distal end of the housing. A capsule having top and bottom seals or septa is configured for fluid engagement with the first and second needle. The capsule may contain a single dose of a secondary medicament. The medicated module may have retention features engaging the capsule. In a more preferred embodiment, the first and second needles pierce the top and bottom seals, respectively, when the medicated module is attached to a drug delivery device. Preferably, the medicated module is aseptically sealed in a separate sterile protective container. The retention cap is preferably configured to move axially in the distal direction when the medicated module is attached to the drug delivery device.

In some cases where priming of the drug delivery system is desirable, the capsule within the medicated module may comprise a bypass to allow medicament from the primary reservoir to flow around the capsule and exit the second needle. The bypass can be any configuration, such as, a channel, pipe, conduit, groove, slot, or any other like pathway that is capable of carrying the medicament from the primary reservoir to the second needle without communicating with the secondary reservoir/medicament. The advantage of such a bypass allows the multi use drug delivery device to be primed and also both the primary and secondary needles to be primed without expelling any of the volume of the secondary medicament. In this case, the seals of the secondary reservoir may be pierced after priming to allow injection of both the primary and secondary medicament. Alternatively, the bypass channel may be used to inject only the primary medicament.

A drug delivery device preferably comprises a primary reservoir of medicament containing at least one drug agent, a dose setter, a dose button, and a delivery mechanism. The dose button may be operably connected to the primary reservoir. The dose setter may be operably connected to the primary reservoir. The delivery mechanism may be of any type, e.g the delivery mechanism may utilize a rotatable piston rod, preferably a rotatable piston rod with two distinct threads.

Moreover, a method of dispensing a fixed dose of one medicament and a variable dose of a primary medicament from separate reservoirs is disclosed that involves the steps of first setting a dose of a first medicament contained in a primary reservoir of a drug delivery device having a single dose setter. Next a dose button is activated that moves the set dose of the first medicament from the primary reservoir in a distal direction and simultaneously forces substantially all of a non-user settable dose (e.g. a single dose) of a second medicament from a sealed capsule having an integral flow distributor, where the capsule is contained in a removable/disposable medicated module, such as those previously described, through a single dispense interface, preferably a hollow injection needle. Upon completion of the delivery procedure substantially all of the second medicament has been expelled as well as the set dose of the first medicament through the single dispense interface. By "substantially all" we mean that at least about 80% of the second medicament is expelled from the capsule preferably at least about 90% is expelled from the capsule. In one arrangement, preferably at least about 80% is delivered within the first 50 micro liters (5 units) flow of the primary medicament.

In a further embodiment, our invention is directed to a drug delivery system to deliver two or more medicaments operable through a single dispense interface. The drug delivery system comprises a primary reservoir of medicament containing at least one drug agent. A dose button is operably connected to the primary reservoir of medicament. The single dispense interface is configured for fluid communication with the primary reservoir. The medicated module contains a capsule comprising a flow distribution system. The flow distribution system may have one, two, or more medicament flow channels. At least one drug agent is contained in the capsule. A single activation of the dose button causes medicament from the primary reservoir and at least one dose of the drug agent from the capsule to be expelled through the single dispense interface. The drug delivery device may comprise a housing containing a single dose setter operably connected to the primary reservoir. The dose of the drug agent from the capsule expelled to through the single dispense interface may be non user-settable. The capsule may contain only a single dose of at least one drug agent.

The primary reservoir of the drug delivery system may be in fluid communication with the capsule. Here, the activation of the dose button may cause medicament from the primary reservoir flow into the secondary reservoir and thereby push out the second medicament from the capsule.

In yet another embodiment, our invention is directed to an injection device where the containment of a secondary drug compound is within a needle sub-assembly (medicated module) containing a capsule (permanent or removable) designed for attachment to an associated primary or master drug delivery device. The actuation of the master device actuates dispense of the secondary drug compound contained in the capsule and a primary drug compound contained in a reservoir in the master drug delivery device. The combination of compounds as discrete units or as a mixed unit is delivered to the body via an integral needle. This would provide a combination drug injection system that, from a user's perspective, would be achieved in a manner that very closely matches the currently available injection devices that use standard needles. One possible delivery procedure would involve the following steps:

1. Attach the medicated needle module to the distal end of the primary injection device (e.g. a threaded hub of a cartridge holder containing a 3 ml cartridge of the primary drug compound) such that the proximal end of the medicated needle is in fluidic communication with the primary compound.
2. Dial up/set the primary injection device such that it is ready to dispense the desired dose of the primary compound.
3. Insert the distal end of the medicated needle into the desired injection site. In some designs, insertion of the medicated needle can trigger delivery of the secondary compound.
4. Dose the primary compound by activating a dose button. This may also cause the secondary compound to automatically dispense.
5. Remove and dispose of the medicated needle module.

The medicated module of our invention can be designed for use with any drug delivery device with an appropriate compatible interface. However, it may be preferable to design the module in such a way as to limit its use to one exclusive primary drug delivery device through employment of dedicated or coded features to prevent attachment of a non-appropriate medicated module to a non-matching injection device. In some situations it may be beneficial from a therapeutic and safety point of view to ensure that the medicated module is exclusive to one drug delivery device (or family of devices) while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound in a way that would prevent the potential risk of double dosing of the secondary compound.

A particular benefit of specific embodiments of our invention is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of our invention, the primary drug delivery device is used more than once and therefore is multi-use. Such a device may or may not have a replaceable reservoir of the primary drug compound, but our invention is equally applicable to both scenarios. It is also possible to have a suite of different medicated modules for various conditions that could be prescribed as one-off extra medication to patients already using a standard drug delivery device. Should the patient attempt to reuse a previously used medicated module, our invention could include features that could alert the patient to this situation. Such means of alerting the user may include some (or all) of the following:
1. Physical prevention of medicated module re-attachment to the primary drug deliver device once the module has been used and removed.
2. Physical prevention of insertion of the used drug dispense interface into the patient (e.g. a single use needle-guard type arrangement).
3. Physical/hydraulic prevention of subsequent liquid flow through the drug dispense interface once it has been used/inserted.
4. Physical locking of the dose setter and/or dose button of the drug delivery device.
5. Visual warnings (e.g. change in color and/or warning text/indicia within an indication window on the module once insertion and/or fluid flow has occurred).
6. Tactile feedback (presence or absence of tactile features on the outer surface of the module hub following use).

A further feature of this embodiment may be that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

Our invention also covers a method of delivering two medicaments stored in separate packages, for example a standard multi-dose glass cartridge and a single dose capsule. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
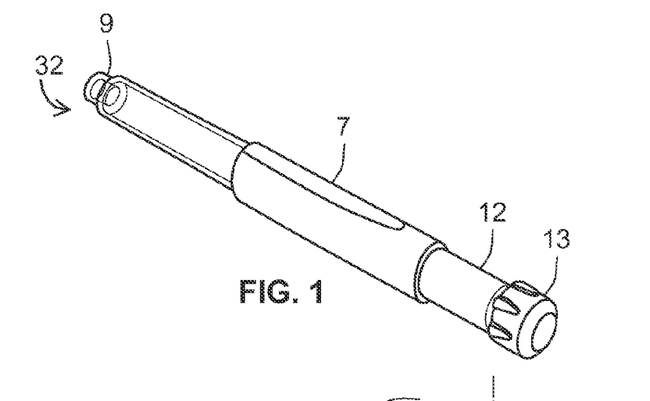
FIG. 1 illustrates one possible drug delivery device that can be used with the medicated module.

Specific embodiments of the disclosed drug delivery device enable administering a fixed predetermined dose of a secondary drug compound (medicament) and a variable dose of a first primary or first drug compound through a single output or drug dispense interface. Setting the dose of the primary medicament by the user automatically determines the fixed dose of the second medicament, which preferably is a single dose contained in a capsule having an integral flow distributor/distribution system. In a preferred embodiment the drug dispense interface is a needle cannula (hollow needle). FIG. 1 illustrates one example of a drug delivery device 7 that the medicated module 4 (see FIGS. 2-4) of our invention can be attached. Each medicated module is preferably self-contained and provided as a sealed and sterile disposable module that has an attachment means 8 compatible to the attachment means at the distal end 32 of drug delivery device 7. Although not shown, the medicated module could be supplied by a manufacturer contained in a protective and sterile container where the user would peel or rip open a seal or the container itself to gain access to the sterile medicated module. In some instances it might be desirable to provide two or more seals for each end of the medicated module.

Figure 2:
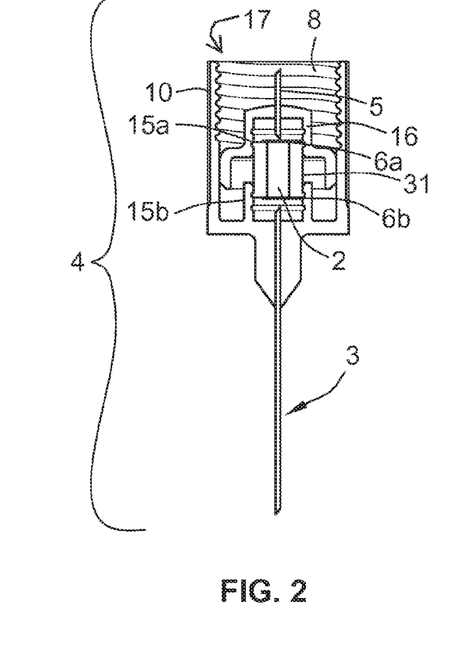
FIG. 2 illustrates an embodiment of the medicated module of the present invention having a self contained reservoir of secondary medicament having two pierceable membranes.
Figure 3:
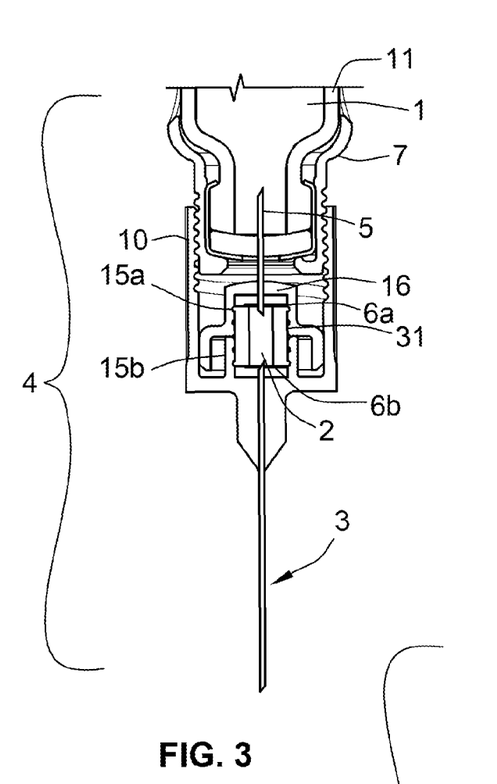
FIG. 3 illustrates an embodiment of the medicated module of the present invention having a self contained reservoir of secondary medicament having two pierceable membranes attached to a delivery.
Figure 4:
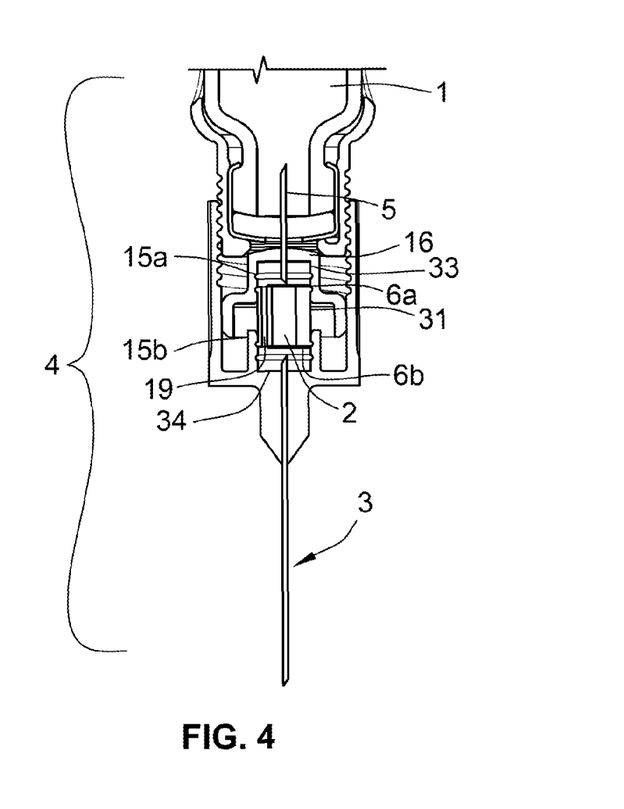
FIG. 4 illustrates an embodiment of the medicated module of the present invention having a self contained reservoir of secondary medicament having two pierceable membranes and a priming bypass.

Any known attachment means can be used to attach the medicated module to the chosen drug delivery device, including all types of permanent and removable connection means, such as threads, snap locks, snap fits, luer locks, bayonet, snap rings, keyed slots, and combinations of such connections. FIGS. 2-4 illustrate the attachment means 8 as screw threads that would engage threads 9 of the distal end 32 of drug delivery device 7. The embodiments shown in FIGS. 2-4 have the benefit of the second medicament 2 as a single dose being contained entirely within capsule 31, hence minimizing the risk of material incompatibility between the second medicament and the materials used in the construction of the medicated module 4, specifically housing 10. This also permits the capsule to be manufactured and assembled as a separate independent sub assembly. The use of the cylindrical pin also significantly assists the filling of the capsule (e.g. fill drug into large diameter opening, insert the cylindrical pin, fit upper seal).

Figure 5:
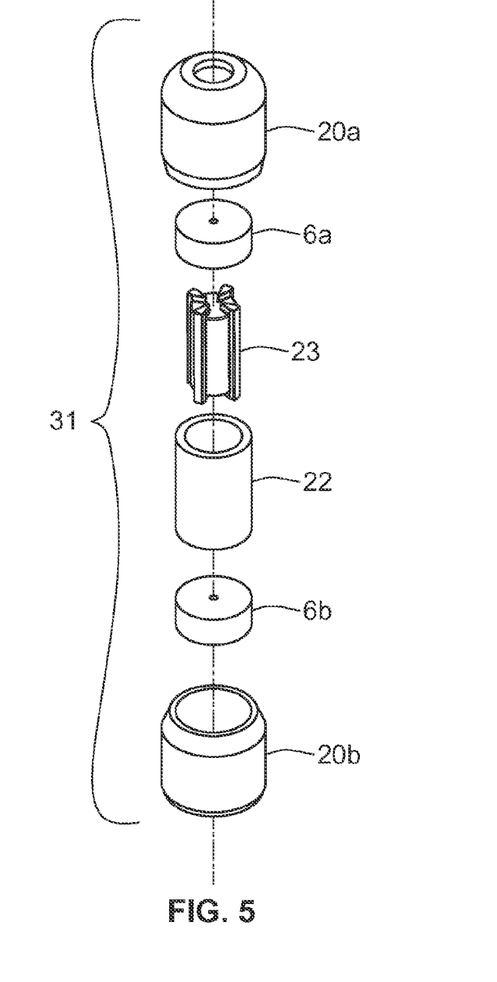
FIG. 5 illustrates a disassembled embodiment of the self contained reservoir within the medicated module of the present invention having an annular flow distributor.

To minimize the residual volume of the second medicament, caused by recirculation and/or stagnant zones, that might remain in capsule 31 at the end of the dispense operation, a flow distributor 23 is located within vial 22 element of capsule 31 (see FIG. 5). The vial, secondary medicament and flow distributor are sealed with septa (or similar, pierceable type seals) 6a and 6b, which are either fixed to the capsule using ferules 20a and 20b, or are retained through other means (e.g. a radial interference bead on the inner diameter of the vial). Preferably the ferules are made from a crimpable material, most preferably metal, such as aluminum. Preferably, the design of flow distributor 23 should ensure that at least about 80% of the second medicament is expelled from capsule 31 through the distal end of needle 3. Most preferably at least about 90% should be expelled. Ideally displacement of the first medicament 1 from the primary reservoir 11 through the capsule 31 into the proximal end of needle 3 will displace the second medicament 2 without substantial mixing of the two medicaments.

Attachment of the medicated module 4 to the multi-use drug delivery device 7 causes the engagement needle 5 located in the proximal end 17 of module 4 to penetrate a septum sealing the distal end of cartridge 11 of the multi-use device 7. Once the engagement needle has passed through the septum of the cartridge, fluid connection is made between the first medicament 1 and the needle 5. The dose of the multi-use device 7 is then set using a dose setter 12 (see FIG. 1) in the normal manner (e.g. by dialing out the appropriate number of units or cocking the device if only a single dose or a fixed dose is possible). The seals containing the secondary medicament are pierced with needles 3 and 5 when the secondary reservoir is moved axially relative to needle 3 (e.g. during attachment, or under the action of a needle guard or similar insertion trigger). Dispense of the medicaments is then achieved by subcutaneously injecting the medicaments via activation of a dose button 13 on device 7. The dose button of our invention can be any triggering mechanism that causes the dose of the first medicament that was set by the dose setter to move distally towards the distal end 32 of the device. In a preferred embodiment the dose button is operably connected to a spindle that engages a piston in the primary reservoir of the first medicament. In a further embodiment the spindle is a rotatable piston rod comprising two distinct threads. The flow distributor contained in the capsule may be used to minimize the risk of mixing occurring between the two medicaments during dispense therefore promoting plug flow. In promoting plug flow it may be desirable to minimize, or preferably prevent change in, cross-sectional area perpendicular to the flow direction where the two medicaments come into contact with each other. While desirable to minimize, or preferably prevent change in, cross-sectional area of the flow channel, the effect of this in a standard needle arrangement would be to increase the length of the flow channel for a fixed volume of the second medicament. This can result in an excessive and unacceptable axial length of the medicated module. Using the flow distributor of our invention may provide a fluid path of minimal cross-sectional area and sufficient length to store the second medicament within an acceptable minimum axial package space.

Embodiments of the medicated module 4 where our invention could be used are illustrated in FIGS. 2-4. In these embodiments the medicated module 4 contains a discrete secondary reservoir or capsule 31 containing a fixed single dose of a secondary medicament 2. In some cases this secondary medicament may be a mixture of two or more drug agents that can be the same or different from the primary drug compound in the drug delivery device 7. Preferably the capsule is permanently positioned within the medicated module and is designed to administer a fixed predetermined dose of a second medicament, however, in some cases it may be preferred to design the module such that the capsule can be removed when empty and replaced with a new capsule.

In the embodiments shown in FIGS. 2-5, capsule 31 has ends that are sealed with pierceable membranes or septa 6a and 6b that provide a hermetically sealed and sterile reservoir for the second medicament. A primary or engagement needle 5 can be displaced axially relative to capsule 31 such that in a depressed position the primary needle 5 will puncture the top membrane 6a. The output needle 3 protrudes above the lower surface of capsule 31 and pierces the lower membrane 6b when the capsule is moved axially relative to needle 3 (e.g. during attachment, or under the action of a needle guard or similar insertion trigger).

During use or attachment of the medicated module to a multi-use drug delivery device, such as the one shown in FIG. 1, the primary needle 5 pierces a septum of cartridge 11 contained in device 7. This attachment causes the retention cap 16 to move distally a predetermined axial displacement so that the retention cap 16 bears against the cartridge causing the retention features 15a and 15b to be overcome and the primary needle to pierce the top membrane 6a of capsule 31. Once the top of the capsule bears against the retention cap, the retention features holding the capsule in the medicated module 4 are overcome and the capsule moves axially downward. Axial movement of capsule 31 causes the proximal end of output needle 3 to pierce lower membrane 6b of capsule 31.

To minimize diffusion of the secondary medicament contained in the capsule within the medicated module into the primary medicament during dispense of the medicaments a flow distributor is included in the capsule. This flow distributor also ensures efficient expulsion of the second medicament from the system, greatly minimizes residual volume, and aids manufacturing/filling of the capsule. Two possible embodiments of the flow distributor are illustrated in FIGS. 6-9 as cylindrical pins. Looking first to FIGS. 6 and 7, cylindrical pin 23 is positioned in vial 22 and configured such that the secondary medicament fills flow channels 27 and 28, which are defined by the shape and location of two or more support ribs 24. In a preferred embodiment the pin is located so that the edges of the flow channel are in direct contact with the inner walls of the vial. In a further embodiment the flow distributor and the vial may be provided as a one-piece component, e.g. as a one-piece molded component. Alternatively the flow distributor and the vial together can be manufactured or assembled as a one-piece component where the flow distributor is integral with the vial. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The flow distributor (cylindrical pin) can be constructed of any material that is compatible to the primary and secondary medicaments. Preferably the vial and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals, and even the flow distributor, that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

Figures 6, 7:
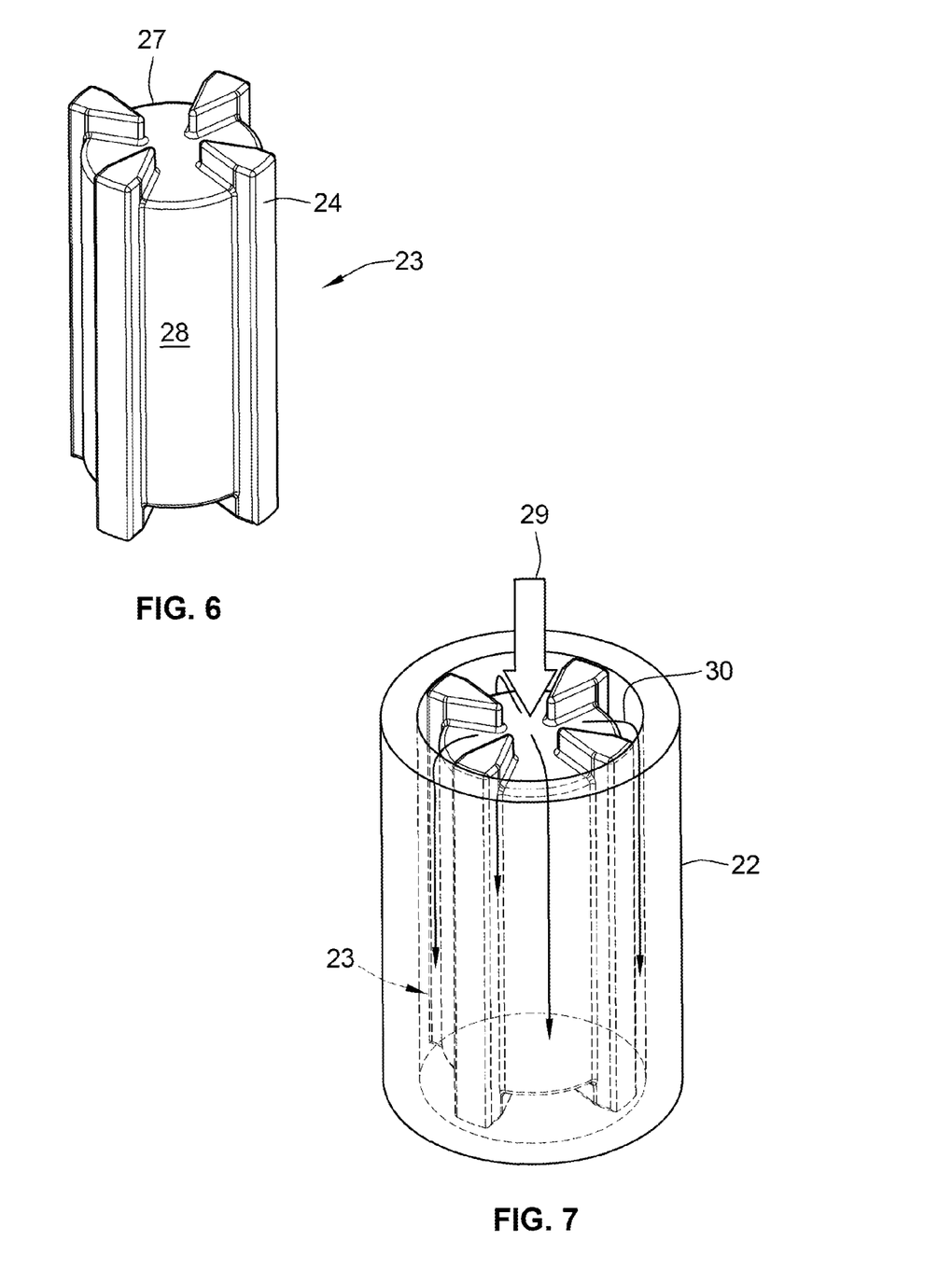
FIG. 6 illustrates a close-up of one embodiment of the annular flow distributor contained in the self contained reservoir within the medicated module of the present invention.
FIG. 7 illustrates medicament flow paths in using one embodiment of the annular flow distributor contained in the self contained reservoir within the medicated module of the present invention.

The shape of the flow channels can be optimized to promote plug flow of medicament, shown by arrows 29 and 30, by varying the dimensions, geometry and number of support ribs 24. The cross-sectional area of the annulus formed between the flow distributor and the wall of the vial should be kept relatively small. The volume available to store the secondary medicament would equal the internal volume of the capsule minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. A further benefit is that as the available volume for medicament is defined by the difference in volumes between the flow distributor and its housing, the external capsule geometry is not dictated by the volume of medicament. As a result, for small volumes of secondary medicament (e.g. 50 micro liters) the capsule can be of an acceptable size for handling, transport, manufacture and assembly. By using different pin geometries it would also be relatively easy to manufacture a range of needles with different fixed dose volumes, without changing the external dimensions of the capsule, and thus with no implications on the rest of the medicated module sub-assembly. As shown in FIG. 7 the flow 30 is initially radial from the needle until the flow reaches the annulus formed between the vial 22 and the cylindrical pin 23.

Preferably, a fluid dynamics computer simulation program, taking into account hydrodynamics and thermodynamics, would be used to obtain the optimum cylindrical pin design. Minimizing or eliminating reverse flow of the secondary medicament within the capsule will greatly enhance the percent expulsion from the system. Removing or reducing an adverse pressure gradient within the capsule can avoid recirculation. This can be accomplished by having a constant cross-section in the capsule to achieve an annular flow pattern. Alternatively, changing the flow direction using radial flow and/or circumferential flow (i.e. swirl) could avoid an adverse pressure gradient. As mentioned, the volume of secondary medicament can be adjusted by manipulating the volume occupied/displaced by the flow distributor.

Figure 8:
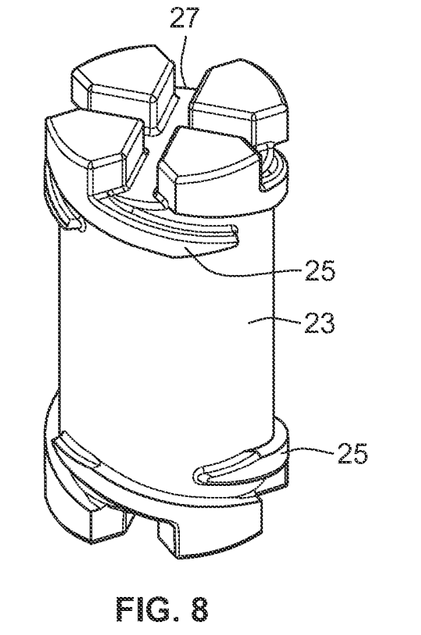
FIG. 8 illustrates a close-up of another embodiment of the annular flow distributor having radial vanes contained in the self contained reservoir within the medicated module of the present invention.
Figure 9:
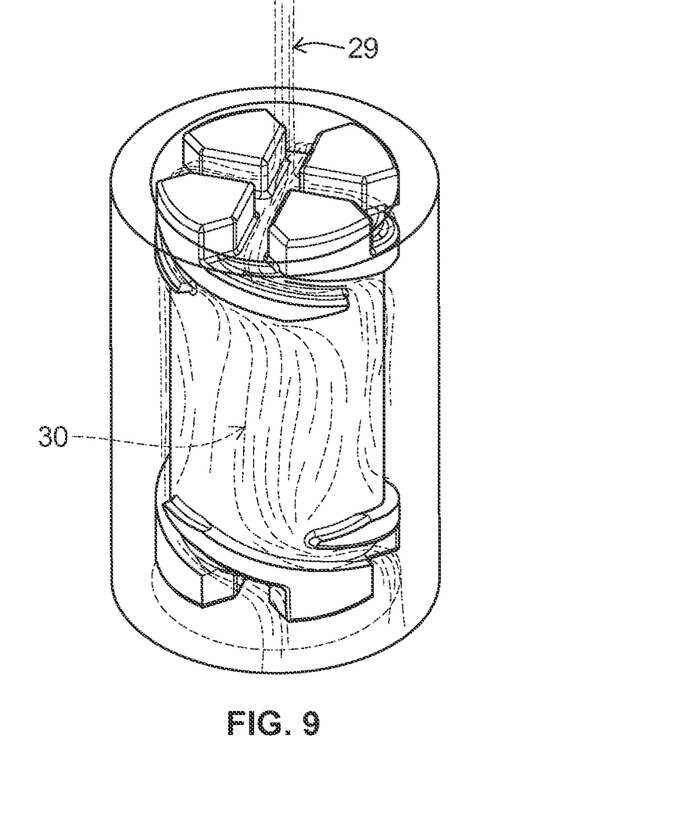
FIG. 9 illustrates theoretical medicament flow paths in using the annular flow distributor illustrated in FIG. 8.
Figure 10:
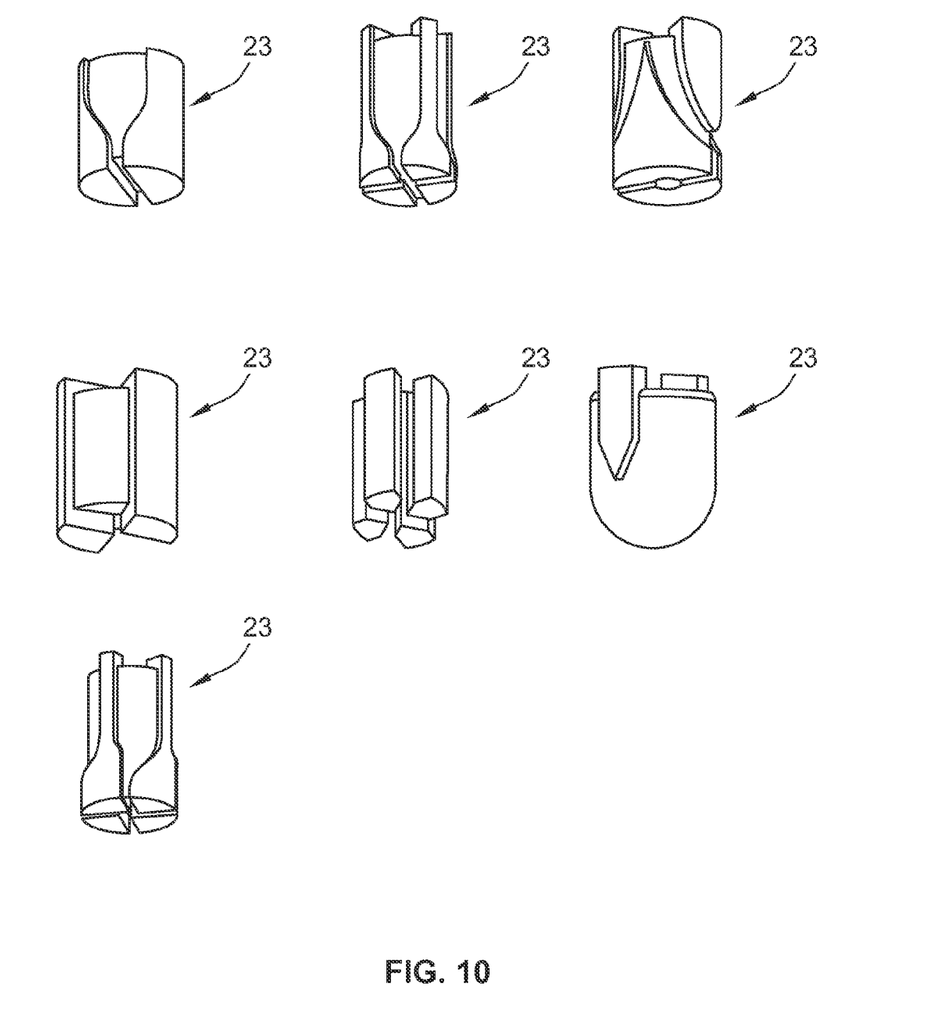
FIG. 10 illustrates a close-up of number of other possible embodiments of the annular flow distributor of the present invention.

To further remove the possibility of stagnant volume at the surface of the lower septa and to reduce the possibility of forming a vortex at the transition between the radial flow portion and the annular flow portion, FIGS. 8 and 9 show another embodiment of cylindrical pin 23 that includes one or more radial vanes 25. In addition, the width of the channels 27 present in the radial flow portion are narrowed to accelerate the flow at the base to help expel the secondary medicament and to reduce the stagnant volume present on the lower septa. Additionally, radial features like these may also help reduce/eliminate medicament loss during the filling process due to splashing as the cylindrical pin is inserted (they would help act like baffle plates to deflect/contain any upward splashing that occurs). FIG. 9 shows a flow pattern through the capsule obtained from computational fluid dynamic modeling. Using the flow distributor shown in FIGS. 8 & 9, computer modeling predicts that less than 5% residual volume of the secondary medicament in the capsule will remain in the capsule after dose delivery, thus achieving about 95% expulsion. FIG. 10 illustrates alternate designs of the flow distributor that could be used in our invention. Of course, as mentioned the flow distribution system could equally comprise a combination of structural components within the medicated module. For example, the inner surface of the vial could be configured with the grooves and ribs to define fluid flow channels and the seals could be configured to assist in changing fluid flow from axial to radial to swirl or vice versa.

In any of the above described embodiments of our invention the second medicament may be either in a powdered solid state, any fluid state contained within the capsule, or coated to the inside surface of the drug dispense interface or cylindrical pin. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

Turning back to FIG. 4, another embodiment of our invention is shown where a bypass channel 19 is incorporated as part of capsule 31 to facilitate priming of output needle 3 with the first medicament 1. Alternatively, the bypass can be used to directly dispense the first medicament 1 without the second medicament 2. When the medicated module 4 of this embodiment is attached to a device, such as the one shown in FIG. 1, the primary needle 5 pierces septum 6a of capsule 31. However, prior to the primary needle piercing the septum the user has the option of initiating priming or primary medicament only dispense operation utilizing bypass channel 19. This is achieved by dispensing the primary medicament into a cavity 33 between the retention cap 16 and the top pierceable membrane 6a. Since the cavity 33 is in fluid communication with bypass channel 19, the primary medicament flows around capsule 31 and into lower cavity 34 and out through output needle 3. After the optional priming operation is complete or performing a direct dispense of the primary medicament, the medicated module can be fully attached (rotated in the case of screw threads) to the multi-use drug delivery device 7 causing the output and primary needles to pierce the lower and top membranes of the reservoir or capsule, respectively. Piercing of membranes 6a and 6b opens fluid communication between the first and second medicaments allowing them to be dispensed through operation of the dispense mechanism on the multi-use device. When this occurs bypass channel 19 is isolated from the contents of capsule 31.

The connection or attachment between the medicated module of the above described embodiments may contain additional features (not shown), such as connectors, stops, splines, ribs, grooves, and the like design features, that ensure that specific medicated module are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the secondary medicament and for attaching one or more needle cannula. The reservoir or capsule can be manufactured from glass or other drug contact suitable material. The integrated injection needle can be any needle cannula suitable for subcutaneous or intramuscular injection.

Additionally, the medicated module could incorporate a safety shield device that would prevent accidental needle sticks and reduces the anxiety experienced by users who suffer from needle phobia. The exact design of the safety shield is not critical to our invention; however, a preferred design is one that is operably connected to the first and/or second reservoirs. In such a design the activation of the safety shield could unlock the drug delivery system and in some cases cause the second medicament to be dispensed prior to activating the dose button to dispense the primary medicament from the first reservoir. It could also be used as the user input/trigger to cause the capsule to be pierced (thereby providing the automatic priming mode function, if desired).

Preferably the medicated module is provided by a manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of our invention may be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose. It can also be a multi-dose device or a single use device.

A typical injection device contains a cartridge or other reservoir of medication. This cartridge is typically cylindrical in shape and is usually manufactured in glass. The cartridge is sealed at one end with a rubber bung and at the other end by a rubber septum. The injection device is designed to deliver multiple injections. The dose button may be any triggering mechanism that causes the dose of the first medicament that was set by the dose setter to move distally towards the distal end of the device. In a preferred embodiment, the dose button is operably connected to a spindle that engages a piston in the primary reservoir of the first medicament. The delivery mechanism is typically powered by a manual action of the user, however, the injection mechanism may also be powered by other means such as a spring, compressed gas or electrical energy. In a further embodiment the spindle is a rotatable piston rod comprising two distinct threads.

In certain embodiments where the medicated module contains a single dose of a medicament, the module may have to be attached to a drug delivery device in order to administer the single dose in the reservoir to a patient. In other words, the medicated module may not be configured to be used as a stand-alone injection device. This is because the module does not have a dose delivery mechanism and instead relies on the dose delivery mechanism contained in the drug delivery device to which it must be attached.

Exemplary embodiments of the present invention have been described. Those skilled in the art will understand, however, that changes and modifications may be made to these embodiments without departing from the true scope and spirit of the present invention, which is defined by the claims.

We claim:

1. A medicated module attachable to a drug delivery device, comprising;
   a. a housing having a proximal end and a distal end, where the proximal end has a connector configured for attachment to a drug delivery device;
   b. a capsule comprising a vial that contains a medicament, where the capsule is encased within the housing and has top and bottom seals;
   c. a distally movable retention cap positioned in the proximal end of the housing;
   d. a first needle fixed in the retention cap;
   e. a second needle fixed within the distal end of the housing, wherein the top and bottom seals are configured for fluid engagement with the first and second needles; and
   f. a flow distribution system contained within the capsule, where the flow distribution system has two or more medicament flow channels, wherein the vial comprises a cylindrical pin and wherein the two or more medicament flow channels are formed between an inner surface of the vial and an outer surface of the pin.

2. The medicated module of claim 1 where the flow distribution system is configured to cause radial flow of medicament.

3. The medicated module of claim 1 where the flow distribution system comprises one or more radial vanes.

4. The medicated module of claim 1 wherein the capsule is replaceable.

5. The medicated module of claim 1 where the capsule contains a liquid medicament.

6. The medicated module of claim 1, further comprising a bypass to allow medicament from a primary reservoir to flow around the capsule and exit the second needle.

7. The medicated module of claim 1, where the flow distribution system and the vial are provided as a one-piece component.

8. The medicated module of claim 7 where the one-piece component is provided as a one-piece molded component.

9. A drug delivery system to deliver two or more medicaments operable through a single dispense interface, comprising;
   a. a primary reservoir of medicament containing at least one drug agent;
   b. a dose button operably connected to the primary reservoir of medicament;
   c. a single dispense interface configured for fluid communication with the primary reservoir; and
   d. a medicated module having a housing with a proximal end, a distal end, and containing a capsule comprising;
     i. top and bottom seals;
     ii. a vial;
     iii. a distally movable retention cap positioned in the proximal end of the housing;
     iv. a first needle fixed in the retention cap;
     v. a second needle fixed within the distal end of the housing, wherein the top and bottom seals are configured for fluid engagement with the first and second needles;
     vi. a cylindrical pin;
     vii. a flow distribution system within the capsule having two or more medicament flow channels, wherein the vial comprises the cylindrical pin and wherein the two or more medicament flow channels are formed between an inner surface of the vial and an outer surface of the pin; and
     viii. at least one drug agent;
   wherein the system is configured such that a single activation of the dose button causes medicament from the primary reservoir and at least one dose of the at least one drug agent from the capsule to be expelled through the single dispense interface.

10. The system of claim 9 where the capsule contains a single dose of the at least one drug agent.

11. The system of claim 9 where the single activation of the dose button causes a non-user settable dose of the drug agent from the capsule to be expelled.

12. The system of claim 9 where at least one of the primary reservoir and the capsule contains a liquid medicament.

13. The system of claim 9 where the primary reservoir is in fluid communication with the capsule.

14. The system of claim 13 wherein the activation of the dose button causes medicament from the primary reservoir to flow into the capsule and thereby push out the at least one drug agent from the capsule.

\* \* \* \* \*